(12) United States Patent
Lin et al.

(10) Patent No.: US 8,909,638 B2
(45) Date of Patent: Dec. 9, 2014

(54) METHOD AND SYSTEM FOR ESTIMATING AGE OF A USER BASED ON MASS DATA

(75) Inventors: Lebin Lin, Shenzhen (CN); Chuan Chen, Shenzhen (CN); Guohui Ling, Shenzhen (CN); Ali Sun, Shenzhen (CN)

(73) Assignee: Tencent Technology (Shenzhen) Company Limited, Shenzhen (CN)

(*) Notice: Subject to any disclaimer, the term of this patent is extended or adjusted under 35 U.S.C. 154(b) by 142 days.

(21) Appl. No.: 13/380,326

(22) PCT Filed: Jun. 23, 2010

(86) PCT No.: PCT/CN2010/074318
§ 371 (c)(1),
(2), (4) Date: Dec. 22, 2011

(87) PCT Pub. No.: WO2011/020371
PCT Pub. Date: Feb. 24, 2011

(65) Prior Publication Data
US 2012/0109973 A1  May 3, 2012

(30) Foreign Application Priority Data

Aug. 21, 2009  (CN) .......................... 2009 1 0042053

(51) Int. Cl.
*G06F 7/00* (2006.01)
*G06F 19/00* (2011.01)
(52) U.S. Cl.
CPC .......... *G06F 19/327* (2013.01); *G06F 19/3443* (2013.01)
USPC ............ 707/736; 707/748; 177/5; 177/25.11; 600/547
(58) Field of Classification Search
None
See application file for complete search history.

(56) References Cited

U.S. PATENT DOCUMENTS

| 5,763,837 | A | * | 6/1998 | Davignon et al. | .......... 174/113 R |
| 7,912,246 | B1 | * | 3/2011 | Moon et al. | .................... 382/103 |
| 2005/0106550 | A1 | * | 5/2005 | Hayashi et al. | ................ 434/362 |
| 2008/0025573 | A1 | | 1/2008 | Nishi et al. | |
| 2008/0294589 | A1 | * | 11/2008 | Chu et al. | .......................... 706/55 |
| 2010/0082360 | A1 | * | 4/2010 | Chien et al. | ........................ 705/1 |
| 2010/0191153 | A1 | * | 7/2010 | Sanders et al. | ................ 600/587 |
| 2012/0051629 | A1 | * | 3/2012 | Ueki et al. | ..................... 382/159 |

FOREIGN PATENT DOCUMENTS

| CN | 101635009 A | 1/2010 |
| JP | 2004-318632 A | 11/2004 |
| JP | 2006-119920 A | 5/2006 |
| JP | 2007-164439 A | 6/2007 |

OTHER PUBLICATIONS

International Search Report (in Chinese with English translation) for PCT/CN2010/074318 mailed Oct. 21, 2010; ISA/CN.

* cited by examiner

*Primary Examiner* — Fred I Ehichioya
*Assistant Examiner* — Hasanul Mobin
(74) *Attorney, Agent, or Firm* — Harness, Dickey & Pierce, P.L.C.

(57) ABSTRACT

A method and a system for determining age of a user based on mass data are provided. The method includes: obtaining basic age data of the user, configuring an initial weight for the basic age data; obtaining an age weight of the user in different kinds of basic age data according to the initial weight and an age similarity of the user in the different kinds of basic age data; and searching the basic age data for an age with a largest age weight, determining the age with the largest age weight as an estimated age of the user. The method and system for determining age of the user based on mass data is able to improve accuracy of the determination of the age of the user.

6 Claims, 3 Drawing Sheets

METHOD AND SYSTEM FOR ESTIMATING AGE OF A USER BASED ON MASS DATA

CROSS-REFERENCE TO RELATED APPLICATIONS

This application is a 371 U.S. National Stage of International Application No. PCT/CN2010/074318, filed Jun. 23, 2010, and claims priority to Chinese patent application No. 200910042053.9, Aug. 21, 2009, the disclosures of which are herein incorporated by reference in their entirety.

FIELD OF THE INVENTION

The present invention relates to mass data processing techniques, and more particularly, to a method and a system for determining age of a user based on mass data.

BACKGROUND OF THE INVENTION

With popularization of the Internet, network has become one indispensable part of people's daily life. The Internet may provide various kinds of services to users, e.g. e-shopping, acquiring information and entertainment. Age is a basic attribute of a user. With respect to users in different ages, different customized Internet services may be provided. However, the uses generally do not fill their real ages on the virtual Internet. Therefore, it has become a problem that how to determine the real age of the user accurately.

Currently, an existing method obtains age data provided by the user and estimates the age of the user through simple boundary value filtering. Specifically, an age range of the users is estimated according to experiences, and values outside of the age range are filtered. Thus, the age of the users are estimated. However, this method relies much on the ages provided by the users, thus is inaccurate.

SUMMARY OF THE INVENTION

Examples of the present invention provide a method for estimating age of a user based on mass data, so as to increase accuracy for determining the age of the user.

Examples of the present invention also provide a system for estimating age of a user based on mass data, so as to increase accuracy for determining the age of the user.

According to an example of the present invention, a method for estimating the age of the user is provided. The method includes:

obtaining basic age data of the user, configuring an initial weight for each kind of basic age data;

obtaining an age weight of the user in each kind of basic age data according to the initial weight and an age similarity of the user in the different kinds of basic age data; and searching the different kinds of basic age data for an age with a largest age weight, estimating the age of the user according to the age with the largest age weight.

According to another example of the present invention, a system for estimating the age of the user is provided. The system includes:

a weight configuring unit, to obtain basic age data of the user and configure an initial weight for each kind of basic age data;

a weight processing unit, communicatively connected with the weight configuring unit, to obtain an age weight of the user in each kind of basic age data according to the initial weight and an age similarity of the user in the different kinds of basic age data; and an age estimating unit, communicatively connected with the weight processing unit, to searching the different kinds of basic age data for an age with a largest age weight, and estimate the age of the user according to the age with the largest age weight.

According to the method and system for determining the age of the user provided by the examples of the present invention, an initial weight is configured for the basic age data, an age weight of the user in different basic age data is obtained according to the initial weight and age similarity of the user in different kinds of basic age data, and the age with the largest age weight is determined as the age of the user. Since the multiple kinds of basic age data provided by the user are evaluated in combination, and the age with the largest age weight is closer to real age of the user. Therefore, the accuracy for determining the age of the user is increased.

DETAILED DESCRIPTION OF THE INVENTION

Figure 1:
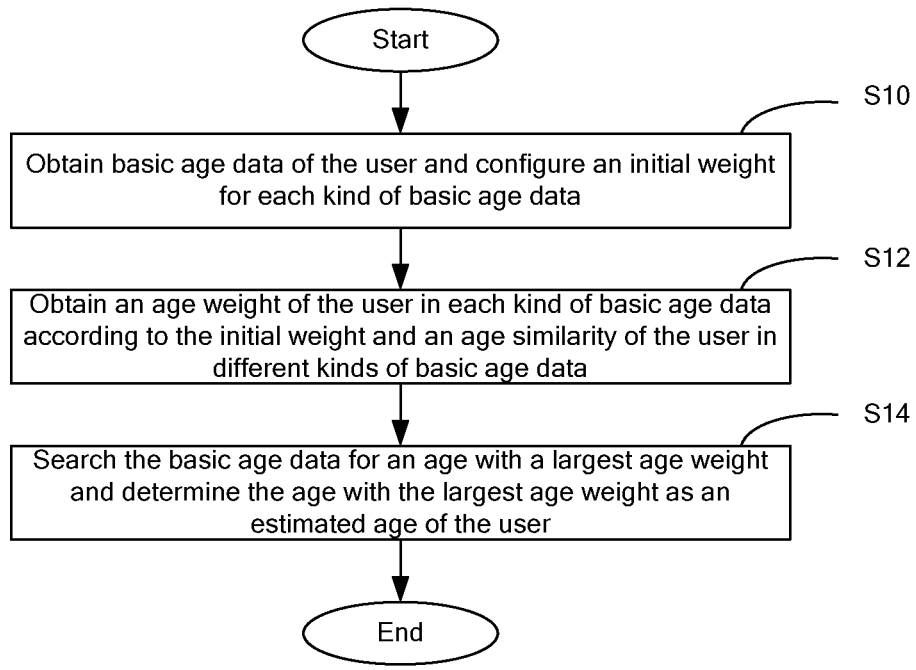
FIG. 1 is a flowchart illustrating a method for determining age of a user based on mass data according to an example of the present invention.

FIG. 1 is a flowchart illustrating a method for determining age of a user based on mass data according to an example of the present invention. The method includes the following steps.

Step S10, basic age data of the user are obtained, and an initial weight is configured for each kind of basic age data, wherein the basic age data are provided by the user when filling information through various kinds of network products, e.g. instant messaging tool or Social Networking Service (SNS), etc.

Figure 2:
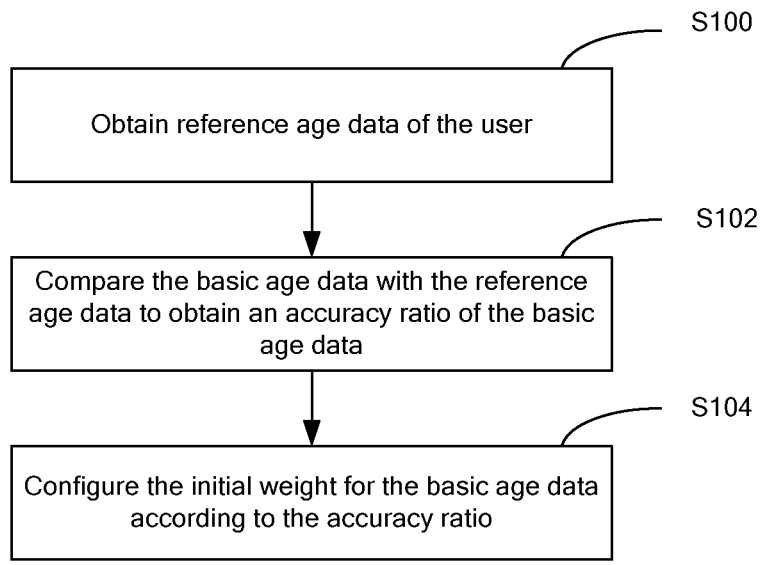
FIG. 2 is a flowchart illustrating a method for configuring an initial weight for the basic age data according to an example of the present invention.

As shown in FIG. 2, in an example of the present invention, the method for configuring the initial weight for the basic age data is as follows.

Step S100, reference age data of the user are obtained.

The reference age data of the user may be obtained through a network questionnaire. Since questions configured by the network questionnaire are relatively precise, the age obtained through the network questionnaire is more accurate than that directly filled by the user.

Step S102, the basic age data are compared with the reference age data, and an accuracy ratio of the basic age data is obtained.

Search each kind of basic age data for users whose ages conform to corresponding reference ages in the reference age data, and divide the number of the users searched out by a total number of users in the user group to obtain the accuracy ratio of the basic age data.

In particular, with respect to each kind of basic age data, search a user group corresponding to the basic age data to obtain the number of users whose basic ages conform to their reference ages in the reference age data. And determine the proportion between this number and the total number of users in the user group corresponding to the basic age data as an accuracy ratio of the kind of basic user data. The term "conform" means that the basic age and the reference age are the same or the difference between them is within a certain range, e.g. 3 years.

Basic age data obtained from different ways belong to different kinds of age data. For example, basic age data obtained through an instant messaging tool belong to one kind of basic age data and basic age data obtained through SNS belong to another kind of basic age data.

Step S104, configure an initial weight for the basic age data according to the accuracy ratio.

In one example, the accuracy ratio of the basic age data has three levels: low, medium and high. Corresponding to the accuracy ratio in the three levels, initial weights configured for the basic age data are respectively P1, P2 and P3. For example, P1=1, P2=5 and P3=9. Suppose that basic age data IM1, IM2, ..., IMn of n users are obtained through the instant messaging tool; basic age data SNS1, SNS2, ..., SNSn of the n users are obtained through SNS, and reference age data R1, R2, ..., Rn of the n users are obtained by questionnaire. Through comparing IM1, IM2, ..., IMn with R1, R2, ..., Rn, it is possible to obtain the accuracy ratio of the basic age data obtained by the instant messaging tool. Suppose this accuracy ratio is low. Then configure the initial weight of the basic age data obtained by the instant messaging tool as P1. Similarly, the accuracy ratio of the basic age data obtained by the SNS can be obtained. Suppose this accuracy ratio is medium. Then the initial weight configured for the basic age data obtained by the SNS is P2.

In another example, it is also possible to configure initial weights for different kinds of basic age data according to sources of the basic age data. For example, age data obtained from registration information of a network service such as alumni record is more accurate. Therefore, the initial weight configured for this kind of basic age data may be relatively high than others.

Step S12, obtain an age weight of the user in each kind of basic age data according to the initial weight of the basic age data and an age similarity of the user in different kinds of basic age data.

Figure 3:
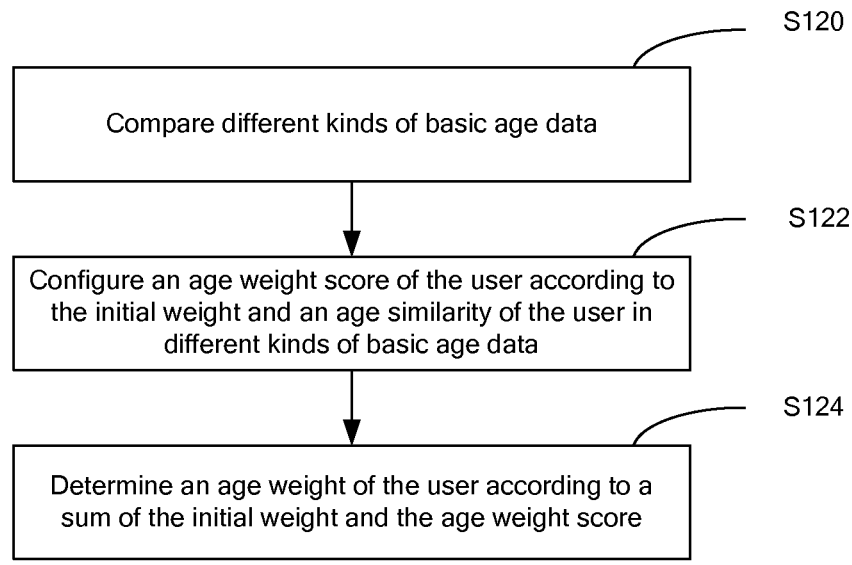
FIG. 3 is a flowchart illustrating a method for obtaining age weights of the user in different kinds of basic age data according to an example of the present invention.

As shown in FIG. 3, in one example of the present invention, the method for obtaining age weights of the user in different kinds of basic age data is as follows.

Step S120, compare different kinds of basic age data. Specifically, with respect to multiple kinds of basic age data obtained through various methods, compare ages of the user in the different kinds of basic age data.

Step S122, configure an age weight score for the user according to the initial weights of different kinds of basic age data and an age similarity of the user in different kinds of basic age data. In one example, the age similarity of the user in different kinds of basic age data may be: same age, similar ages and different ages, wherein the age similarity of similar ages means that the difference between the ages is within 3 years, and the age similarity of different ages means that the difference between the ages is larger than 3 years. Compare the initial weights of different kinds of basic age data to obtain a weight relationship between the basic age data. The weight relationship may be: same weight, similar weights and different weights, wherein the weight relationship of same weight means that the two kinds of basic age data have the same weight level (i.e. both of them are high, medium or low); the weight relationship of similar weights means that weights of the two kinds of basic age data have a difference of one level (i.e. the two weight levels are high and medium, or medium and low); the weight relationship of different weights means that the weights of the two kinds of basic age data have a difference of two levels (i.e. the weights are high and low). In one example, age weight scores of the user are configured as table 1.

| Weight relationship | Age similarity | | |
|---|---|---|---|
| | Same age | similar ages | Different ages |
| Same weight | +A1 | +A4 | 0 |
| Similar weights | +A2 | +A5 | 0 |
| Different weights | +A3 | +A6 | 0 |

For example, A1 = 1, A2 = 2, A3 = 3, A4 = 4, A5 = 5 and A6 = 6.

Step S124, determine an age weight of the user according to a sum of the initial weight and the age weight score. In the above example, compare different kinds of basic age data. As to each kind of basic age data, obtain a weight relationship between it and each other kind of basic age data and an age similarity of the user under the weight relationship. The age weight score of the user in the basic age data is the sum of all age weight scores obtained by comparing the basic age data with other basic age data.

In one example, three kinds of basic age data of the user is M, N and O. In the example, suppose the initial weights of the three kinds of basic age data are respectively P1, P2 and P3. With respect to three users a, b and c, suppose the ages of the three users in the basic age data M are respectively Ma, Mb and Mc, the ages of the three users in the basic age data N are respectively Na, Nb and Nc, and the ages of the three users in the basic age data O are respectively Oa, Ob and Oc. Compare the basic age data M, N and O. Suppose the weights of the basic age data M and the basic age data N are similar, the weights of the basic age data M and the basic age data O are different, and the weights of the basic age data N and the basic age data O are similar. As to user a, suppose Ma=25, Na=25 and Oa=23, i.e. Ma and Na have the same age, Ma and Oa have similar ages, and Na and Oa have similar ages. According to the age weight scores configured in table 1, it is obtained that the age weight of Ma is P1+A2+A6, the age weight of Na is P2+A2+A5, and the age weight of Oa is P3+A6+A5. Similarly, the age weights of user b and user c may be obtained following the above method.

Step S14, search different kinds of basic age data for an age with a largest age weight, determine the age with the largest age weight as an estimated age of the user. In the above example, as to user a, determine the age with the largest age weight among Ma, Na and Oa as the estimated age of user a. Since the age with the largest age weight is closer to the real age of the user, the age is determined more accurately.

In one example, after obtain the estimated age of the user, compare the age weight of the estimated age and initial weight. Classify the age weight of the estimated age of the user into one of three levels: high weight, medium weight and low weight. In one example, suppose the initial weights of three kinds of basic age data are P1, P2 and P3. If the age weight of the estimated age is smaller than or equal to P2, the age weight is low. If the age weight of the estimated age is larger than P2 but is smaller than or equal to P3, the age weight is medium. If the weight of the estimated age is larger than P3, the age weight is high.

Figure 4:
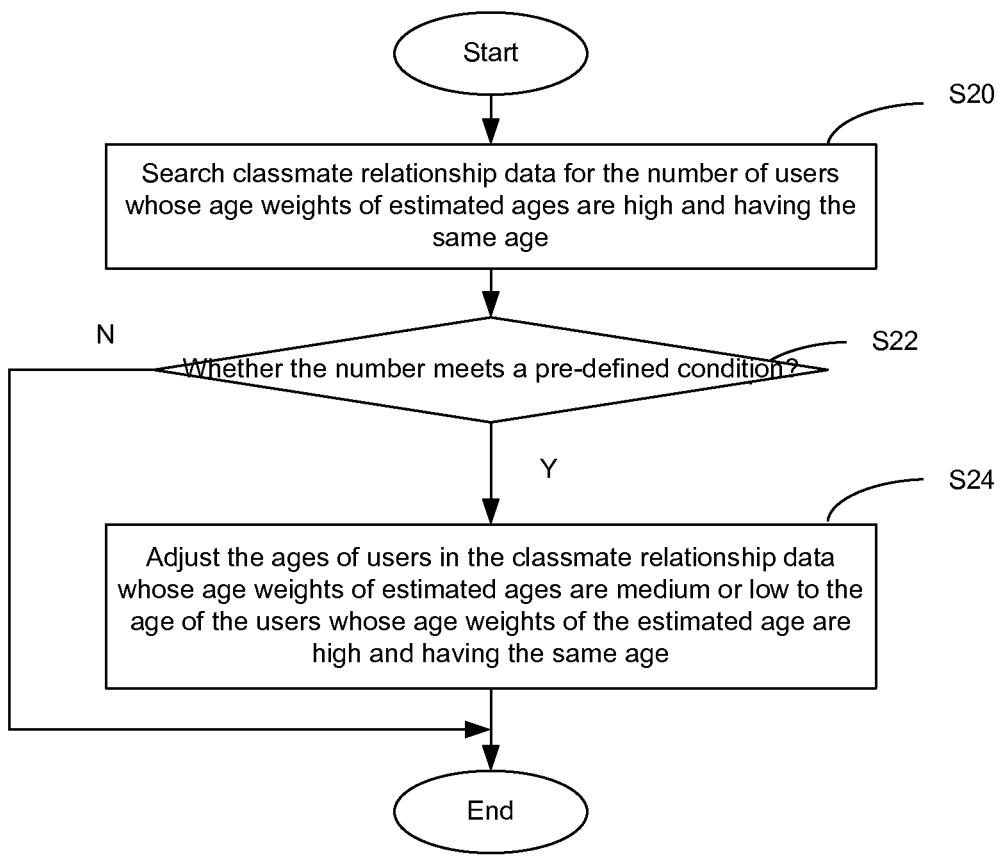
FIG. 4 is a flowchart illustrating a method for determining the age of the user according to classmate relationship data according to an example of the present invention.

FIG. 4 is a flowchart of a method for determining age of a user according to classmate relationship data according to an example of the present invention. The method includes the following steps.

Step S20, search classmate relationship data for the number of users whose age weights of estimated ages are high and have the same estimated age. The classmate relationship data is a collection of data of users having classmate relationship. Users having the classmate relationship usually have the same or similar ages. The classmate relationship data may be obtained from classmate group members and a friend group of the user.

Step S22, determine whether the number meets a re-defined condition. If the number meets the pre-defined condition, proceed to step S24; otherwise, the procedure ends. In one example, the pre-defined condition is: m>3 and m/n>=¼, wherein m denotes the number of users whose age weights of the estimated ages are high and having the same estimated age, n denotes a total number of users in the classmate relationship.

Step S24, adjust estimated ages of uses whose age weights of the estimated ages are medium or low in the classmate relationship to be the estimated age of the users whose age weights of the estimated age are high and having the same estimated age. In one example, if the number of users whose age weights of the estimated age are high and having the same estimated age meets the above pre-defined condition, since the estimated ages of these users are more accurate and ages of users in the classmate relationship are usually the same or similar, the ages of the users whose age weights are low or medium are adjusted according to the estimated age of the users whose age weights are high. Thus, the estimated ages are more accurate.

Figure 5:
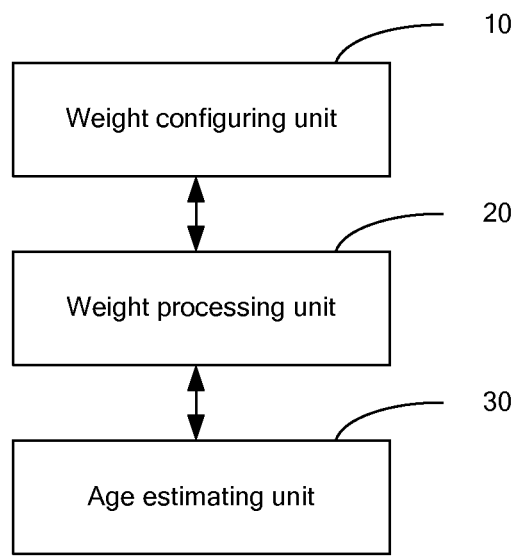
FIG. 5 is a schematic diagram illustrating a structure of a system for determining the age of a user based on mass data according to an example of the present invention.

FIG. 5 is a schematic diagram illustrating a structure of a system for determining age of a user based on mass data according to an example of the present invention. As shown in FIG. 5, the system includes: a weight configuring unit 10, a weight processing unit 20 and an age estimating unit 30.

The weight configuring unit 10 is to obtain basic age data of the user and configure an initial weight for each kind of basic age data.

The weight processing unit 20 is communicatively connected with the weight configuring unit 10, to obtain an age weight of the user in each kind of basic age data according to the initial weight and an age similarity of the user in different kinds of basic age data.

The age estimating unit 30 is communicatively connected with the weight processing unit 20, to search the basic age data for an age with a largest age weight, and determine the age with the largest age weight as the estimated age of the user.

Figure 6:
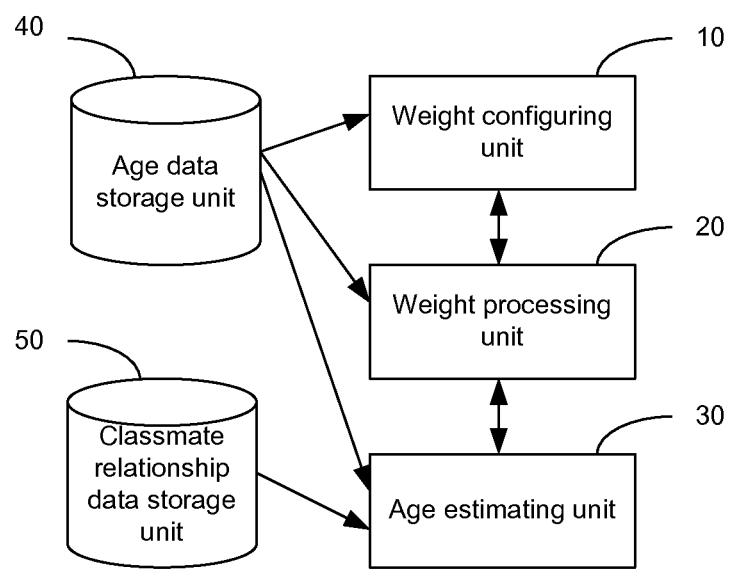
FIG. 6 is a schematic diagram illustrating a structure of a system for determining the age of a user based on mass data according to another example of the present invention.

FIG. 6 is a schematic diagram illustrating another structure of a system for estimating age of a user based on mass data according to an example of the present invention. As shown in FIG. 6, besides the weight configuring unit 10, the weight processing unit 20 and the age estimating unit 30, the system further includes an age data storage unit 40 and a classmate relationship data storage unit 50.

The age data storage unit 40 is communicatively connected with the weight configuring unit 10, the weight processing unit 20 and the age estimating unit 30, to store the basic age data and reference age data. The basic age data are provided by the user through various kinds of network products. And the reference age data are obtained by network questionnaire. Since questions configured by the questionnaire are relatively precise, the reference age data are more accurate than the basic age data.

The classmate relationship data storage unit 50 is communicatively connected with the age estimating unit 30, to store the classmate relationship data. Users having the classmate relationship usually have the same or similar ages. It is possible to obtain the classmate relationship data from classmate group members or a friend group of the user.

In one example, the weight configuring unit 10 is further to obtain the reference age data of the user, compare the basic age data with the reference age data, obtain an accuracy ratio of the basic age data, configure the initial weight for the basic age data according to accuracy ratio. It is possible to search each kind of basic age data to find users whose basic ages conform to the reference ages. The accuracy ratio is obtained by dividing the number of users whose basic ages conform to the reference ages by the total number of users. The weight configuring unit 10 is further to classify the accuracy ratio into three levels: high, medium and low, and configure the initial weight for the basic age data according to different levels of accuracy ratios.

In one example, the weight processing unit 20 is further to compare the basic age data, configure an age weight score of the user according to the initial weight and an age similarity of the user in different kinds of basic age data. The age weight of the user is the sum of the initial weight and the age weight score. The weight processing unit 20 compares different kinds of basic age data, as to each kind of basic age data, obtains a weight relationship between it and another basic age data and an age similarity of the user under the weight relationship. The age weight score of the user in the basic age data is the sum of all the age weight scores obtained by comparing the basic age data and other basic age data. After the weight processing unit 20 calculates the age weight, the age estimating unit 30 searches for an age with the largest age weight and determines the age with the largest age weight as the estimated age of the user.

In one example, after the age estimating unit 30 determines the estimated age of the user, the weight processing unit 20 compares the age weight of the estimated age and the initial weight, and classifies, according to the determined result, the age weight of the estimated age into at least three levels: high weight, medium weight and low weight.

In one example, the age estimating unit 30 is further to search the classmate relationship data for users whose age weights of the estimated age are high and having the same age, determine whether the number of the users searched out meets a pre-defined condition, if yes, modify the age of the users in the classmate relationship whose age weights are medium or low to be the estimated age of the users whose age weights of the estimated age are high and having the same age. In one example, the pre-defined condition is: m>3 and m/n>=¼, wherein m denotes the number of users whose age weights of the estimated age is high and having the same age in the classmate relationship data, n denotes a total number of users in the classmate relationship. Since the ages of users in the classmate relationship are usually the same or similar, the ages of the users whose age weights are low or medium are adjusted according to the estimated age of the users whose age weights are high. Thus, the estimated ages are more accurate.

What has been described and illustrated herein is a preferred example of the disclosure along with some of its variations. The terms, descriptions and figures used herein are set forth by way of illustration only and are not meant as limitations. Many variations are possible within the spirit and scope of the disclosure, which is intended to be defined by the following claims—and their equivalents—in which all terms are meant in their broadest reasonable sense unless otherwise indicated.

What is claimed is:

1. A method for estimating age of a user, comprising:

obtaining different kinds of basic age data of the user from network products that include an instant messaging tool and a Social Networking Service (SNS), wherein the different kinds of basic kinds of basic age data are provided by the user by filling in ages through the different kinds of network products, configuring an initial weight for each kind of basic age data according to an accuracy ratio of the basic age data;

obtaining an age weight of the user in each kind of basic age data according to a sum of the initial weight and an age weight score of the kind of basic age data; wherein the age weight score of the kind of basic age data is configured according to the initial weight of the kind of basic age data and an age similarity of the user in different kinds of basic age data; and searching the different kinds of basic age data for the basic age data with a largest age weight, estimating the age of the user according to the basic age data with the largest age weight;

wherein the configuring the initial weight for each kind of basic age data comprises:

obtaining reference age data of the user through the network questionnaire, comparing the basic age data with the reference age data to obtain an accuracy ratio of the basic age data; and configuring the initial weight for the basic age data according to the accuracy ratio; and wherein the accuracy ratio of the basic age data comprises searching the basic age data for the selected group of users whose ages conform to the reference age data, dividing the number of the users searched out by the total number of users in the basic age data, and determining the divided result as the accuracy ratio of the basic age data.

2. The method of claim 1, wherein the configuring the initial weight for each kind of basic age data comprises:

configuring the initial weight for each kind of basic age data according to a source of the basic age data.

3. The method of claim 1, further comprising:

obtaining an estimated age of the user in classmate relationship data, and adjusting estimated ages of other users in the classmate relationship data according to estimated age of the user and the age weight of the user.

4. The method of claim 1, further comprising:

comparing the age weight of the estimated age of the user and the initial weight, classifying, according to a compared result, the age weight of the estimated age into three levels: high weight, medium weight and low weight.

5. The method of claim 4, further comprising:

searching classmate relationship data for users whose age weights of estimated age are high and having the same age, determining whether the number of the user searched out meets a pre-defined condition, if the number meets the pre-defined condition, adjusting ages of users in the classmate relationship data whose age weights of estimated ages are medium and low to the estimated age of the users whose age weights of the estimated age are high and having the same age.

6. The method of claim 3, further comprising:

searching classmate relationship data for users whose age weights of estimated age are high and having the same age, determining whether the number of the user searched out meets a pre-defined condition, if the number meets the pre-defined condition, adjusting ages of users in the classmate relationship data whose age weights of estimated ages are medium and low to the estimated age of the users whose age weights of the estimated age are high and having the same age.

* * * * *